United States Patent
Hassan

(10) Patent No.: US 9,770,509 B2
(45) Date of Patent: *Sep. 26, 2017

(54) SELF MICRO-EMULSIFYING DRUG DELIVERY SYSTEM WITH INCREASED BIOAVAILABILITY

(71) Applicant: Pharmaceutics International, Inc., Hunt Valley, MD (US)

(72) Inventor: Emadeldin Hassan, Hunt Valley, MD (US)

(73) Assignee: Pharmaceutics International, Inc., Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/802,837

(22) Filed: Jul. 17, 2015

(65) Prior Publication Data

US 2015/0320864 A1 Nov. 12, 2015

Related U.S. Application Data

(62) Division of application No. 13/989,687, filed as application No. PCT/US2010/058106 on Nov. 24, 2010.

(51) Int. Cl.
| | | |
|---|---|---|
| *A61K 31/03* | (2006.01) | |
| *A61K 47/22* | (2006.01) | |
| *A61K 9/107* | (2006.01) | |
| *A61K 9/48* | (2006.01) | |
| *A61K 47/14* | (2017.01) | |

(52) U.S. Cl.
CPC ............ *A61K 47/22* (2013.01); *A61K 9/1075* (2013.01); *A61K 9/4858* (2013.01); *A61K 47/14* (2013.01)

(58) Field of Classification Search
None
See application file for complete search history.

(56) References Cited

U.S. PATENT DOCUMENTS

| 4,918,103 | A | 4/1990 | Park et al. | |
|---|---|---|---|---|
| 7,670,618 | B2 * | 3/2010 | Patel ................... | A61K 9/0095 424/451 |
| 2004/0092428 | A1 | 5/2004 | Chen et al. | |
| 2006/0051462 | A1 | 3/2006 | Wang | |
| 2009/0004261 | A1 * | 1/2009 | Breul ................... | A61K 31/415 424/455 |
| 2010/0291191 | A1 * | 11/2010 | Shoichet .............. | A61K 9/0024 424/450 |
| 2013/0317117 | A1 | 11/2013 | Hassan | |

FOREIGN PATENT DOCUMENTS

| EP | 2 255 786 A1 | 12/2010 |
|---|---|---|
| EP | 2 435 022 B1 | 4/2014 |
| WO | WO 2010/136952 A2 | 12/2010 |

OTHER PUBLICATIONS

U.S. Appl. No. 13/989,687, filed May 2013, Hassan.*
Borhade et al., "Design and Evaluation of Self-Microemulsifying Drug Delivery System (SMEDDS) of Tacrolimus," *AAPS PharmSciTech*, 9(1): 13-21 (Mar. 2008).
United States Patent and Trademark Office, International Search Report with respect to PCT/US2010/058106 (Feb. 8, 2011).
International Bureau of WIPO, International Preliminary Report on Patentability with respect to PCT/US2010/058106 (Jun. 6, 2013).
*Handbook of Green Chemicals*, Second Edition, Ash et al. (Ed.), p. 275 (2004).

* cited by examiner

*Primary Examiner* — Svetlana M Ivanova
(74) *Attorney, Agent, or Firm* — Leydig, Voit & Mayer, Ltd.

(57) ABSTRACT

The invention provides a formulation comprising (a) a drug that is poorly water-soluble, (b) at least one surfactant, and (c) at least one polar lipid, wherein the formulation is substantially free of a polar solvent, as well as methods of preparing the formulation and methods of increasing the bioavailability of a drug using the formulation.

7 Claims, No Drawings

SELF MICRO-EMULSIFYING DRUG DELIVERY SYSTEM WITH INCREASED BIOAVAILABILITY

CROSS-REFERENCE TO RELATED APPLICATIONS

This patent application is a divisional of U.S. patent application Ser. No. 13/989,687, filed Aug. 13, 2013, which is the U.S. national phase of International Application No. PCT/US2010/058106, filed Nov. 24, 2010, the disclosure of which is incorporated by reference.

BACKGROUND OF THE INVENTION

Many drugs are poorly soluble in water. Due to their low solubilities, these drugs have a correspondingly low degree of bioavailability. Therefore, it would be advantageous and desirable to have a method of increasing the dissolution and bioavailability of poorly water-soluble drugs.

BRIEF SUMMARY OF THE INVENTION

The invention provides a formulation for delivery of one or more poorly water-soluble drugs, wherein the formulation comprises (a) a drug that is poorly water-soluble, (b) at least one surfactant, and (c) at least one polar lipid, wherein the formulation is substantially free of a polar solvent.

DETAILED DESCRIPTION OF THE INVENTION

Poorly water-soluble drug delivery systems, such as traditional self micro-emulsifying drug delivery systems (SMEDDS), require the use of polar solvents (e.g., isopropanol or propylene glycol). In contrast, the inventive embodiment excludes the use of a polar solvent. In particular, the invention provides a formulation for delivery of one or more poorly water-soluble drugs, wherein the formulation comprises (a) a drug that is poorly water-soluble, (b) at least one surfactant, and (c) at least one polar lipid, wherein the formulation is substantially free of a polar solvent. Examples of polar solvents include, but are not limited to, water, methanol, acetic acid, acetone, isopropanol, propylene glycol, and ethyl acetate.

For the purposes of describing the invention, the term "substantially free" refers to less than 5% (e.g., less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.5%, less than 0.1%, or 0%) (w/w) of the formulation.

For the purposes of describing the invention, the term "drug" refers to any compound which is biologically active, e.g., exhibits a therapeutic or prophylactic effect in vivo, or a biological effect in vitro. The term "poorly water-soluble" as used in conjunction with the present invention encompasses the terms sparingly water-soluble, slightly or very slightly water-soluble, and practically or totally water-insoluble compounds. A compound is poorly water-soluble for the purposes of this invention if it requires at least 30 parts solvent to dissolve one part solute.

Any poorly water-soluble drug, or combination of drugs including at least one poorly water-soluble drug, can be used in the inventive formulation. Suitable drugs include, but are not limited to, antihypertension drugs, antibiotic drugs, and anticancer or antitumor drugs. Examples of suitable drugs include, but are not limited to, peptides, nifedipine, glibencalmide, indomethacin, ursodeoxycholic acid, diphenyl hydrantoin, biphenyl dimethyl dicarboxylate, geldanamycin, mitotane, fenofibrate, simvastatin, idebenone, and camptothecin. In one embodiment of the invention, the poorly water-soluble drug is not mitotane.

Any surfactant or combinations of surfactants (e.g., combinations of 2, 3, 4, 5, 6, 7, 8, 9, 10, or more surfactants) can be used in the inventive formulation. Suitable surfactants include nonionic, cationic, and anionic surfactants that can be synthetic or natural. Surfactants for use in the invention may include, but are not limited to, ammonium lauryl sulfate, sodium lauryl sulfate (SDS), sodium laureth sulfate, also known as sodium lauryl ether sulfate (SLES), sodium myreth sulfate, dioctyl sodium sulfosuccinate, perfluorooctanesulfonate (PFOS), perfluorobutanesulfonate, alkyl ether phosphate, sodium stearate, sodium lauroyl sarcosinate, perfluorononanoate, perfluorooctanoate (PFOA or PFO), octenidine dihydrochloride, permanently charged quaternary ammonium cation, cetyl trimethylammonium bromide (CTAB) (i.e., hexadecyl trimethyl ammonium bromide), cetyl trimethylammonium chloride (CTAC), cetylpyridinium chloride (CPC), polyethoxylated tallow amine (POEA), benzalkonium chloride (BAC), benzethonium chloride (BZT), 5-bromo-5-nitro-1,3-dioxane, dimethyldioctadecylammonium chloride, dioctadecyldimethylammonium bromide (DODAB), CHAPS (3-[(3-cholamidopropyl)dimethylammonio]-1-propanesulfonate), cocamidopropyl hydroxysultaine, cocamidopropyl betaine, lecithin, cetyl alcohol, stearyl alcohol, cetostearyl alcohol (consisting predominantly of cetyl and stearyl alcohols), oleyl alcohol, octaethylene glycol monododecyl ether, pentaethylene glycol monododecyl ether, polyoxypropylene glycol alkyl ethers, glucoside alkyl ethers, decyl glucoside, lauryl glucoside, octyl glucoside, polyoxyethylene glycol octylphenol, Triton X-100, polyoxyethylene glycol alkylphenol ethers, Nonoxynol-9, glyceryl laurate, polysorbates like polysorbate 20 (Tween™20, Span™20), polysorbate 40 (Tween™40, Span™40), polysorbate 60 (Tween™60, polysorbate 65 (Tween™65, Span™65), polysorbate 80 (Tween™80, Span™80), sorbitan alkyl esters, cocamide MEA, cocamide DEA, dodecyl dimethylamine oxide, and block copolymers of polyethylene glycol and polypropylene glycol.

Any polar lipid or combination of polar lipids (e.g., combinations of 2, 3, 4, 5, 6, 7, 8, 9, 10, or more polar lipids) can be used in the inventive formulation. Suitable polar lipids include mono- and di- glycerides, esters of fatty acids, and polysilane esters. Specific examples include propylene glycol monocaprylate (Capryol®90), propylene glycol monolaurate, propylene glycol oleate, propylene glycol myristate, propylene glycol monostearate, propylene glycol hydroxy stearate, propylene glycol ricinoleate, propylene glycol isostearate, propylene glycol monooleate, propylene glycol dicaprylate/dicaprate, propylene glycol dioctanoate, propylene glycol caprylate/caprate, propylene glycol dilaurate, propylene glycol distearate, propylene glycol dicaprylate, and propylene glycol dicaprate (Captex®100).

The at least one surfactant and at least one polar lipid can each be present in the formulation in an amount of 10-90% (e.g., 20%, 30%, 40%, 50%, 60%, 70%, or 80% or ranges thereof, such as 10-30%, 15-20%, 15-17%, 20-60%, 35-50%, or 38-42%) weight/volume (w/w). In other words, the at least one surfactant can be present in the formulation in an amount of 10-90% (w/w) and the at least one polar lipid (e.g., two polar lipids) can be present in the formulation in an amount of 10-90% (w/w). For example, the inventive formulation can comprise 10-30% (w/w) of a first polar lipid, 20-60% (w/w) of a second polar lipid, and 10-30% (w/w) of a surfactant.

In one embodiment the first polar lipid is propylene glycol monocaprylate, the second polar lipid is propylene glycol dicaprate, and the surfactant is a polysorbate, such as polysorbate 20, polysorbate 40, polysorbate 60, polysorbate 65, polysorbate 80, or mixtures thereof. Preferably, the polysorbate is polysorbate 80 (i.e., polyoxyethylene sorbitan monooleate). Accordingly, a particular example of the inventive formulation includes 10-30% (w/w) propylene glycol monocaprylate, 20-60% (w/w) propylene glycol dicaprate, and 10-30% (w/w) polysorbate (e.g., polysorbate 80). A second particular example of the inventive formulation includes 15-20% (w/w) propylene glycol monocaprylate, 35-50% (w/w) propylene glycol dicaprate, and 15-20% (w/w) polysorbate (e.g., polysorbate 80). A third particular example of the inventive formulation includes 15-17% (w/w) propylene glycol monocaprylate, 38-42% (w/w) propylene glycol dicaprate, and 15-17% (w/w) polysorbate (e.g., polysorbate 80).

The inventive formulation makes it possible to load a large amount of drug (e.g., at least 20%, at least 25%, at least 30%, at least 35%, at least 40%, at least 45%, at least 50%, at least 55%, at least 60%, at least 65%, at least 70%, or more). In particular, the inventive formulation has a drug loading of at least 33%, preferably between 33% and 67%, and more preferably between 37% and 54%. In one embodiment, the formulation comprises 1 mg to 800 mg (e.g., 2 mg, 5 mg, 10 mg, 20 mg, 40 mg, 50 mg, 60 mg, 100 mg, 200 mg, 300 mg, 400 mg, 500 mg, 600 mg, or 700 mg) of the drug.

The emulsion globules of the formulation are generally less than about 200 nm (e.g., less than about 180 nm, less than about 150 nm, less than about 120 nm, less than about 100 nm, less than about 90 nm, less than about 80 nm, less than about 70 nm, or less than about 60 nm) in diameter. The small size globules formed in the GI tract are designed to result in higher bioavailability of the drug compared to tablet formulations.

The inventive formulation (e.g., pharmaceutical formulation) also can comprise a carrier (e.g., a pharmaceutically acceptable carrier). The carrier can be any suitable carrier or mixture of carriers. For example, the pharmaceutically acceptable carrier can be any of those conventionally used and is limited only by chemico-physical considerations, such as solubility and lack of reactivity with the active compound (s), as well as by the route of administration. Preferably, the pharmaceutically acceptable carrier is chemically inert to the active compound (s) and has no detrimental side effects or toxicity under the conditions of use. Suitable pharmaceutically acceptable carriers, for example, vehicles, adjuvants, excipients, and diluents, are well-known in the art and are readily available.

The inventive formulation can be packaged in any pharmaceutical composition for oral administration. Suitable compositions that comprise the formulation are capsules, including hard gelatin capsules or soft gelatin capsules. Soft gelatin capsules are made with a gelatin shell, optionally in association with plasticizers, such as glycerine and/or sorbitol. Capsule forms can be of the ordinary hard- or soft-shelled gelatin type containing, for example, surfactants, lubricants, and inert fillers, such as lactose, sucrose, calcium phosphate, and corn starch. The composition also can be formulated as a liquid suspension for administration directly into a patient's mouth. Alternatively, the formulation can be packaged into a solid dosage form (e.g., in a state readily converted to a microemulsion in vivo, thereby enhancing the dissolution of the drug).

Additional components that can be present in the dosage form include, but are not limited to, lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, and flavoring agents.

The inventive formulation can be used for any suitable purpose. For example, the inventive formulation can be used for scientific and research purposes, such as in determining the types of diseases or disorders, particularly cancers, which can be treated and for which their onset can be delayed, or progression slowed, by administration of the inventive formulation. The inventive formulation can be used in vitro in conjunction with cultured cells, tissues, organs, and the like.

The formulation can be used to deliver a drug to a host and has particular usefulness in applications in vivo. For example, the inventive formulation can be used in the prevention, delay of onset, slowing, or treatment of the progression of a disease or disorder, such as cancer.

The inventive method of delivering a drug to a host, especially an animal such as a mammal (e.g., mouse, rat, guinea pig, hamster, rabbit, cat, dog, pig, cow, horse, or simian, such as a human), comprises administering the inventive formulation to a host. Preferably, the inventive formulation is administered in an amount effective to treat or prevent a disease or disorder in the host (e. g., a therapeutically or prophylatically effective amount).

The method of delivering a drug to a host through administering the formulation of the invention can be made more effective in the treatment or prevention of disease by using it in conjunction with other known methods of treating or preventing diseases or disorders. For example, when the poorly water-soluble drug in the inventive formulation is an anticancer or antitumor drug, the formulation can be administered in conjunction with (i.e., sequentially or concurrently) with other anticancer or antitumor compounds, such as doxorubicin, bleomycin, vincristine, vinblastine, VP-16, VW-26, cisplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

One skilled in the art will appreciate that suitable methods of administering the inventive formulation to a host are known in the art, and, although more than one route can be used to administer a particular composition, a particular route can provide a more immediate and more effective reaction than another route. Accordingly, the described methods are merely exemplary and are in no way limiting.

The dose administered to the host should be sufficient to prevent the targeted disease or disorder, e. g., cancer, delay its onset, slow its progression, or treat the disease or disorder (e. g., reverse or negate the condition). One skilled in the art will recognize that dosage will depend upon a variety of factors including the strength of the particular drug(s)

employed, as well as the age, species, condition, and body weight of the host. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

The invention also provides for a method for producing the inventive formulations using standard techniques, such as those set forth in the Example, as well as a method of increasing the bioavailability of a drug that is poorly water-soluble comprising preparing the inventive formulations.

The following example further illustrates the invention but, of course, should not be construed as in any way limiting its scope.

EXAMPLE

This example demonstrates the preparation of a Self Micro-Emulsifying Drug Delivery System (SMEDD) for mitotane (250 mg) soft gelatin capsule. Although the experiments described below employ mitotane as the water-soluble drug, one of ordinary skill in the art will appreciate that the inventive formulation can comprise any poorly water-soluble drug.

Development studies were performed to maximize drug loading in the dosage form while providing a system that was physically stable upon dilution with 20% weight/weight water, while minimizing the globule size upon 1:200 dilution with 0.01 N HCl or water, as determined by light scattering analysis.

After initial solubility screening, four formulations were developed. These formulations contained medium chain triglycerides, polar lipids, and surfactants. Drug loading of 25% was achieved in systems containing Capryol™ 90 (Propylene Glycol Monocaprylate, Type II), Captex® 100 (Propylene Glycol Dicaprate), and Labrasol® (Caprylocaproyl Macrogolglycerides); as well as Triethyl Citrate, Captex® 100, and Labrasol®. Generally, at 25% drug loading, the systems containing either Capryol™ 90 or Triethyl Citrate dispersed immediately upon dilution into a homogenous solution, and displayed minimum (or no) oily residue before and after centrifugation.

However, as drug loading was increased from 25% to 50%, the emulsions were increasingly unstable. For some systems at the highest drug loading, precipitates formed immediately upon dilution. In other cases, dispersion was delayed and/or a pellet was formed upon centrifugation.

In order to achieve a higher stable drug concentration within the selected solvents/systems, Polysorbate 80 was used to replace Labrasol® as the system surfactant. Polysorbate 80 enhanced dispersion and reduced globule sizes in the Capryol™ 90 system to a greater degree than in the Triethyl Citrate system. From these results, formulations containing Capryol™ 90, Captex® 100, and Polysorbate 80; in different proportions were selected for further development.

TABLE 1

Qualitative Formula of Mitotane SMEDDS Soft Gelatin Capsules

| Item Number | Material | Function |
|---|---|---|
| 1. | Gelatin USP/NF (150 Bloom Limed Bone, Type B) | Gelatin Shell |
| 2. | Glycerin, USP 99.7% | Plasticizer |
| 3. | Sorbitol, 76% solution (Sorbitol Special ™) | Plasticizer |
| 4. | Purified Water, USP | Solvent |
| 5. | FD&C Blue #1 | Colorant |
| 6. | Opatint White (G-18000) | Colorant |
| 7. | Mitotane | Active Pharmaceutical Ingredient (API) |
| 8. | Propylene Glycol Monocaprylate, Type II, NF (Capryol ™ 90) | Solubilizing Agent |
| 9. | Propylene Glycol Dicaprate (Captex ® 100) | Solubilizing Agent |
| 10. | Polysorbate 80, USP/NF | Surfactant |

TABLE 2

Quantitative Formula of Gelatin Mass for Mitotane Soft Gel Capsules (250 kg Batch)

| Item Number | Ingredients | % weight/weight | Batch Quantity (kg) |
|---|---|---|---|
| 1. | Gelatin USP/NF (150 Bloom Limed Bone, Type B) | 42.00 | 105.0 |
| 2. | Glycerin, USP 99.7% | 3.00 | 7.500 |
| 3. | Sorbitol, 76% solution (Sorbitol Special ™) | 18.00 | 45.00 |
| 4. | Purified Water, USP* | 34.92* | 104.8* |
| 5. | FD&C Blue #1 | 0.08 | 0.200 |
| 6. | Opatint White (G-18000) | 2.00 | 5.000 |
| | TOTAL | 100.0 | 267.5 |

*Purified Water, USP includes a 7% excess (17.5 kg) of the 250 kg batch size, in order to compensate for evaporation during the manufacturing process.

TABLE 3

Quantitative Fill Solution Formula for Mitotane SMEDD Soft Gel Capsules, 250 mg

| Item Number | Ingredient | mg/capsule | % weight/weight | Batch Quantity (kg) |
|---|---|---|---|---|
| 7. | Mitotane | 250.0 | 28.50 | 2.625 |
| 8. | Propylene Glycol Monocaprylate, Type II, NF (Capryol ™ 90) | 138.1 | 15.75 | 1.450 |
| 9. | Propylene Glycol Dicaprate (Captex ® 100) | 350.8 | 40.00 | 3.684 |
| 10. | Polysorbate 80, USP/NF | 138.1 | 15.75 | 1.450 |
| | TOTAL | 877.0 | 100.0 | 9.209 |

Abbreviated manufacturing procedures included the following:

1. Fill Solution

Mix Capryol™90, Captex® 100, and Polysorbate 80, NF until a homogenous solution is obtained Heat to 45° C.±5° C.

Slowly add mitotane into mixing solution, continue mixing until completely dissolved Deaerate final solution 2. Gelatin Mass
   Reserve approximately 3 kg of water
   Mix remaining water, Sorbitol Special™, and Glycerin
   Heat to 85° C.±5° C.; add gelatin
   Maintain temperature at 85° C.±5° C. with continuous mixing until gelatin granules are completely dissolved, cook gelatin
   In separate container, mix Opatint White and FD&C Blue #1
   Add colorant mixture to gelatin mixture, rinse colorant container with reserved water and add to gelatin mixture
   Continue mixing until uniform color is obtained
   Deaerate the gel mass
   Determine water content of gel mass; adjust if needed (water addition or continued heating)
   Transfer to holding tank, maintain at 55°, use within 96 hours
3. Encapsulation
   Encapsulate using size "20" oblong die roll
   Tumble dry the capsules
   Tunnel dry the capsules
   Inspect
   Polish
   Pack into bulk containers
Final Package into 100 count, 150 mL, HDPE bottles with heat seal caps.
4. Tentative Processing Parameter Targets
   Average Fill Weight: 877 mg±3%
   Ribbon Thickness: 0.81 mm±0.05 mm
   Tailing Edge Seam Thickness: NLT 0.25 mm
   Drying Conditions: 24° C. (21° C. to 28° C.); 20% Relative Humidity (12% to 26%)
   Drying End Point Moisture Content: ≥2% and ≤8% by LOD of capsule shell
   Formulation Development included the following:
   Solubility: Solubility in Single Solvents was determined either by incremental loading or by direct mixing.
   Incremental loading is an addition of small portions of drug to a specific volume of solvent with mixing and gentle heating. Quantities of drug are listed below in two columns, with the highest weight of drug that dissolved in the "Soluble" column, and the lowest weight that did not dissolve listed in the "Precipitated" column. Although this method does not yield a maximum solubility of the drug in the solvent, it does give sufficient information to screen potential solvents for use in formulation.
   Solvents of interest are then screened with direct loading of the drug in specific intermediate amounts, and are reported below in the same manner.
   Drug loading screening studies are reported in grams of mitotane dissolved per volume of solvent. This screening method provides a quick evaluation of potentially useful solvents without correcting for the density of the individual solvents.

TABLE 4

Initial Solvent Screening Studies

| Vehicle/Solvent | Soluble (Clear Solutions after Mixing, g/mL) | Insoluble (Precipitant observed, g/mL) |
| --- | --- | --- |
| Capmul MCM | Not tested | 0.250 |
| Capryol™ 90 | 0.550 | 0.670 |
| Captex® 100 | 0.500 | 0.550 |
| Captex® 200 | 0.563 | 0.580 |
| Cremophor® EL | 0.449 | 0.469 |
| Ethanol | 0.553 | 0.570 |
| Labrafil® | 0.479 | 0.492 |
| Labrasol® | 0.550 | 0.651 |
| Miglyol Oil 812N | 0.500 | 0.591 |
| Poloxamer 124 | 0.189 | 0.204 |
| Polyethylene Glycol 400 | 0.235 | 0.255 |
| Polyethylene Glycol 600 | 0.345 | 0.365 |
| Polysorbate 20 | 0.428 | 0.445 |
| Polysorbate 80 | 0.475 | 0.495 |
| Propylene Glycol | 0.132 | 0.149 |
| Soybean Oil | Not tested | 0.250 |
| Triethyl Citrate | 0.750 | 0.837 |

Single vehicle solutions were selected at 50% drug loading for accelerated stability testing at 40° C./75% RH. These solutions were analyzed for assay and related substances at initial, two weeks, and four weeks.

TABLE 5

Stability Results of Single Vehicles Solutions at 50% Drug Load

| Single Vehicles | Batch Number | Initial Assay (% label claim) | 2 Weeks 40° C./ 75% RH Assay | 4 Weeks 40° C./ 75% RH Assay |
| --- | --- | --- | --- | --- |
| Capryol™ 90 | F-2772-018A | 82.0 | 99.2 | 97.7 |
| Captex® 100 | F-2772-018B | 90.0 | 77.1 | 77.4 |
| Labrasol® | F-2772-018C | 99.0 | 98.7 | 97.0 |

Solvent Systems Solubility was then determined by selection of the solvents with the higher solubility, and combining them with materials of the types and ratios generally appropriate for production of SMEDD. The combinations below were tested either by incremental loading or by direct mixing, and are reported in the same manner as the single solvents. This screening method provides a quick evaluation of potentially useful solvent systems without correcting for the density of each solvent system as would be needed for reporting mitotane percent weight in each system.

TABLE 6

Solvent System Screening Studies

| Solvent System (weight ratio) | Clear Solutions after Mixing (g/mL) | Precipitated (g/mL) |
| --- | --- | --- |
| Capmul MCM:PEG 400:Polysorbate 80 (1:1:1) | Not tested | 0.604 |
| Capryol™ 90:Captex® 100 (1:1) | 0.620 | 0.670 |

TABLE 6-continued

Solvent System Screening Studies

| Solvent System (weight ratio) | Clear Solutions after Mixing (g/mL) | Precipitated (g/mL) |
|---|---|---|
| Capryol ™ 90:Captex ® 100:Labrasol ™ (56:22:22) | 0.550 | 0.600 |
| Capryol ™ 90:Captex ® 100:Labrasol ™ (3:1:1) | 0.550 | 0.600 |
| Capryol ™ 90:Labrafil ®:Labrasol ™ (1:1:1) | 0.527 | 0.546 |
| Capryol ™ 90:Labrasol ™ (1:1) | 0.520 | 0.570 |
| Capryol ™ 90:Labrasol ™:Captex ® 100 (56:22:22) | 0.550 | 0.620 |
| Capryol ™ 90:Labrasol ™:Soybean Oil (1:1:1) | Not tested | 0.687 |
| Capryol:Captex ® 100:Labrasol ™ (1:1:1) | 0.550 | 0.803 |
| Captex ® 100:Capryol ™ 90:Labrasol ™ (56:22:22) | 0.550 | 0.600 |
| Captex ® 100:Labrasol ™ (1:1) | 0.550 | 0.570 |
| Captex ® 100:Labrasol ™:Capryol ™ 90 (56:22:22) | 0.620 | 0.670 |
| Labrasol ™:Capryol ™ 90:Captex ® 100 (2:1:1) | 0.600 | 0.650 |

Temperature dependent stability of selected mitotane solvents and solvent systems was explored by observing selected systems at 5° C. and at room temperature for 24 hours.

Temperature Cycling of Selected Solvents and Solubility Systems was studied. Systems were prepared at ambient temperature, with mixed solvent in the weight ratios reported in brackets. Mitotane, 0.25 grams, was then added to 1 gram of each solvent or solvent mixture. Samples were placed in the refrigerator (5° C.±3° C.) and observations were recorded. The samples were then left at ambient temperature for 24 hours, and observations recorded. The samples were then placed in a 40° C. oven, and final observation was made after another 24 hours. These observations are recorded in the table below.

Water Tolerance was evaluated since water migration often occurs as the fill solution is exposed to wet gelatin mass during the soft gelatin encapsulation process. Therefore, portions of water were added to the mitotane solutions to determine if they would precipitate upon exposure to quantities of water that typically may migrate into the capsule fill solution.

Solvent systems were prepared at ambient temperature, with mixed solvent in the weight ratios reported in brackets in the table below. Mitotane was then added to 3 grams of each solvent or solvent mixture. (For the samples reported as 25% Drug loading, 0.75 grams of mitotane was added to the 3 grams of solvent. For samples reported as 50% Drug loading, 1.5 grams were added to 3 grams of solvent.) After the mitotane solution was obtained, 300 milligrams of water was added to the sample with vortex mixing. If the sample remained as a clear solution, a second portion of 300 milligrams of water was added and mixing repeated. (If the sample precipitated after the first addition, a second addition of water was not performed.)

TABLE 7

Physical Stability of Mitotane Solutions at 5° and Room Temperature

| Vehicle/System (w/w) | Drug Loading (g Drug/g Solvent) | 5° C. (minimum 24 hours) | Room Temperature (minimum 24 hours) |
|---|---|---|---|
| Capmul MCM | 0.25 | Precipitate | Clear Solution |
| Capmul MCM:PEG 400:Polysorbate 80 (1:1:1) | 0.25 | Clear Solution | Clear Solution |
| Capryol ™ 90 | 0.50 | Clear Solution | Clear Solution |
| Capryol ™ 90:Captex ® 100 (1:1) | 0.25 | Clear Solution | Clear Solution |
| Capryol ™ 90:Captex ® 100:Labrasol ™ (1:1:1) | 0.50 | Clear Solution | Clear Solution |
| Capryol ™ 90:Captex ® 100:Labrasol ™ (56:22:22) | 0.50 | Clear Solution | Not Tested |
| Capryol ™ 90:Captex ® 100:Labrasol ™ (2:2:1) | 0.25 | Clear Solution | Clear Solution |
| Capryol ™ 90:Labrasol ™:Captex ® 100 (2:2:1) | 0.25 | Clear Solution | Clear Solution |
| Capryol ™ 90:Captex ® 100:Polysorbate 80 (1:1:1) | 0.25 | Clear Solution | Clear Solution |
| Capryol ™ 90:Captex ® 100:Polysorbate 80 (1:1:1) | 0.40 | Clear Solution | Clear Solution |
| Capryol ™ 90:Captex ® 100:Polysorbate 80 (22:56:22) | 0.40 | Clear Solution | Clear Solution |
| Capryol ™ 90:Labrasol ™:Soybean Oil (1:1:1) | 0.25 | Clear Solution | Clear Solution |
| Captex ® 100 | 0.50 | Clear Solution | Clear Solution |
| Captex ® 100:Capryol ™ 90:Labrasol ™ (56:22:22) | 0.50 | Clear Solution | Not Tested |
| Labrafil ® | 0.25 | Clear Solution | Clear Solution |
| Labrasol ™ | 0.50 | Clear Solution | Clear Solution |
| Labrasol ™:Capryol ™ 90:Captex ® 100 (56:22:22) | 0.50 | Clear solution | Not Tested |
| Miglyol Oil 812N | 0.25 | Clear Solution | Clear Solution |
| Polyethylene Glycol 600 | 0.25 | Clear Solution | Clear Solution |
| Polysorbate 20 | 0.25 | Clear Solution | Clear Solution |
| Polysorbate 80 | 0.25 | Clear Solution | Clear Solution |
| Soybean Oil | 0.25 | Precipitate | Clear Solution |
| Triethyl Citrate | 0.25 | Clear Solution | Clear Solution |

TABLE 8

Water Tolerance of Mitotane Solutions

| Vehicle/System (w/w) | Drug Loading* | Appearance following addition of 10%* w/w water | Appearance following addition of 20%* w/w water |
|---|---|---|---|
| Capmul MCM | 25% | Hazy liquid | Not tested |
| Capmul MCM:PEG 400:Polysorbate 80 (1:1:1) | 25% | Hazy liquid | Not tested |
| Capryol ™ 90 | 50% | Hazy, precipitation | Not tested |
| Capryol ™ 90:Captex ® 100 (1:1) | 25% | Hazy, precipitation | Not tested |
| Capryol ™ 90:Captex ® 100:Labrasol ™ (1:1:1) | 50% | Hazy liquid | Not tested |
| Capryol ™ 90:Captex ® 100:Labrasol ™ (56:22:22) | 50% | Hazy, precipitation | Not tested |
| Capryol ™ 90:Captex ® 100:Labrasol ™ (2:2:1) | 25% | Hazy, precipitation | Not tested |
| Capryol ™ 90:Labrasol ™:Captex ® 100 (2:2:1) | 25% | Hazy liquid | Not tested |
| Capryol ™ 90:Labrasol ™:Soybean Oil (1:1:1) | 25% | Hazy, precipitation | Not tested |
| Captex ® 100 | 50% | Immiscible/precipitation | Not tested |
| Captex ® 100:Capryol ™ 90:Labrasol ™ (56:22:22) | 50% | Hazy, precipitation | Not tested |
| Captex ® 200 | 25% | Immiscible/precipitation | Not tested |
| Labrafil ® | 25% | Hazy/precipitation | Not tested |
| Labrasol ™ | 50% | Hazy liquid | Not tested |
| Labrasol ™:Capryol ™ 90:Captex ® 100 (56:22:22) | 50% | Hazy, precipitation | Not tested |
| Miglyol Oil 812N | 25% | Hazy, precipitation | Not tested |
| Polyethylene Glycol 600 | 25% | Clear liquid | Clear liquid |
| Polysorbate 20 | 25% | Clear yellow liquid | Clear yellow liquid |
| Polysorbate 80 | 25% | Clear yellow liquid | Clear yellow liquid |
| Soybean Oil | 25% | Hazy, precipitation | Not tested |
| Triethyl Citrate | 25% | Hazy liquid | Not tested |

*Percent relative to the weight of solvent in the sample, not the total weight of sample.

Dilution of Mitotane Systems

Mitotane systems were tested in a 1:200 dilution (v/v) with purified water, USP or N/100 HCl. Mitotane systems (1.0 mL) were charged into 200 mL of either purified water, USP or N/100 HCl, with continuous mixing for five minutes. Samples were transferred in a glass jar. Liquids were then centrifuged for 30 minutes at 5000 rpm to prepare a pellet (if present). Drug loading ranged from 25% to 50%.

Differential Scanning Calorimetry (DSC)

After dilutions were centrifuged, pellets were evaluated using DSC. The testing method used in the evaluation of the pellets was 25° C. to 85° C.

TABLE 9

Differential Scanning Calorimetry of Mitotane Dilutions (Pellets)

| System (w/w) | Drug Loading | Media | Onset (° C.) | Peak (° C.) |
|---|---|---|---|---|
| Capryol ™ 90:Captex ® 100:Labrasol ™ (56:22:22) | 50% | Purified Water, USP | 72.91 | 80.17 |
| Capryol ™ 90:Captex ® 100:Labrasol ™ (56:22:22) | 50% | 0.01N HCl | 54.81 | 70.85 |
| Captex ® 100:Capryol ™ 90 Labrasol ™ (56:22:22) | 50% | Purified Water, USP | 31.78 | 74.92 |
| Captex ® 100:Capryol ™ 90 Labrasol ™ (56:22:22) | 50% | 0.01N HCl | 70.32 | 80.79 |
| Labrasol ™:Capryol ™ 90:Captex ® 100: (56:22:22) | 50% | Purified Water, USP | 43.39 | 66.38 |
| Labrasol ™:Capryol ™ 90:Captex ® 100: (56:22:22) | 50% | 0.01N HCl | 57.79 | 66.26 |

Note:
No pellets formed from Capryol ™ 90:Captex ® 100:Labrasol ™ (1:1:1), with either dilulent.

Dynamic Light Scattering of Mitotane Dilutions

The supernatant liquids decanted after centrifugation were evaluated using a Nicomp ZLS Particle Sizer for Dynamic Light Scattering. DLS was tested to evaluate the globule size in the supernatant liquids. Samples were examined for two minutes at an intensity set point of approximately 300 KHz.

Formulation Selection

Based on these studies, several formulations were prepared (see Tables 10 and 11). Temperature cycling was tested to evaluate the physical stability of the three formulations F-2772-054 (33.3% drug w/w), F-2772-055 (20.0% drug w/w), and F-2772-057 (33.3% drug w/w) as well as formulations F-2772-054 and 057 at 28.5% drug w/w. F-2772-056 was eliminated because of the amount of precipitate. Temperature cycling consisted of three stages for 24 hour periods; refrigeration (5° C.), 40° C. conventional oven, and room temperature. After each 24 hour cycle, solutions were evaluated for clarity. Formulations containing 28.5% drug w/w remained in solution after temperature cycling showing the solutions were physically stable.

TABLE 10

Mitotane Formulations

| Item No. | System (w/w) | Drug Loading | Intensity Diameter (Gaussian) nm |
|---|---|---|---|
| 1. | Capryol ™ 90:Captex ® 100:Labrasol ™ (1:1:1) | 25% | 149.49 (Water) 251.24 (0.01N HCl) |
| 2. | Capryol ™ 90:Captex ® 100:Labrasol ™ (56:22:22) | 25% | 246.63 (Water) 399.85 (0.01N HCl) |
| 3. | Capryol ™ 90:Captex ® 100:Polysorbate 80 (1:1:1) | 50% | 93.68 (Water) 81.03 (0.01N HCl) |
| 3B. | Capryol ™ 90:Captex ® 100:Polysorbate 80 (1:1:1) | 25% | 120.82 (Water) 138.62 (0.01N HCl) |
| 4. | Capryol ™ 90:Captex ® 100:Polysorbate 80 (56:22:22) | 50% | 104.48 (Water) 143.95 (0.01N HCl) |
| 5. | Capryol ™ 90:Captex ® 100:Polysorbate 80 (22:56:22) | 25% | 547.98 (Water) 640.09 (0.01N HCl) |
| 6. | Capryol ™ 90:Captex ® 100:Polysorbate 80 (22:56:22) | 50% | 125.84 (Water) 138.68 (0.01N HCl) |

TABLE 11

Mitotane Formulations

| | Formulation | | |
|---|---|---|---|
| Ingredient (s) | F-2772-054 % w/w | F-2772-055 % w/w | F-2772-057 % w/w |
| Mitotane | 28.5 | 20.0 | 28.5 |
| Capryol ™ 90 | 23.8 | 26.7 | 15.7 |
| Captex ® 100 | 23.8 | 26.7 | 40.0 |
| Polysorbate 80 | 23.8 | 26.7 | 15.7 |
| TOTAL | 100.0 | 100.0 | 100.0 |
| Density (g/cm$^3$) | 1.05 | 1.03 | 1.04 |
| Assay by External Std. | 99.8 | 99.5 | 97.3 |

SUMMARY

Drug loading of 25% wt/wt was achieved in systems containing a mixture of Capryol™ 90, Captex® 100, and Labrasol™ as well as a mixture containing Triethyl Citrate, Captex® 100, and Labrasol™. These systems dispersed immediately upon dilution (1:200, water or dilute HCl) into a homogenous suspension, and displayed minimum (or no) oily residue before and after centrifugation, indicating an appropriate ratio of ingredients for SMEDDS formation.

In trials to achieve a stable, higher drug concentration, Polysorbate 80 was used in addition to and as a replacement for Labrasol™ as the system surfactant. Addition of Polysorbate 80 enhanced dispersion and reduced globule sizes in the Capryol™ 90 system, however this system was found to be an unstable.

TABLE 12

Observations upon Dilution of Mitotane Systems

| System (expressed as w/w) | Drug Loading | Dilution (1:200 v/v) | Observations after Dilution | Observations after Centrifugation |
|---|---|---|---|---|
| Capryol ™ 90:Captex ® 100:Labrasol ™, (1:1:1) | 25% | Purified Water, USP | Milky white liquid, immediate emulsion | No pellet formation, no oily residue |
| Capryol ™ 90:Captex ® 100:Labrasol ™, (1:1:1) | 25% | 0.01N HCl | Milky white liquid, immediate emulsion | No pellet formation, no oily residue |
| Capryol ™ 90:Captex ® 100:Labrasol ™, (1:1:1) | 30% | Purified Water, USP | Cloudy white liquid, immediate dispersion | Drug crystals- rod shaped side of the tube (very few crystals) |
| Capryol ™ 90:Captex ® 100:Labrasol ™, (1:1:1) | 30% | 0.01N HCl | Cloudy white liquid, immediate dispersion, oily residue | Drug crystals- rod shaped side of the tube (very few crystals) |
| Capryol ™ 90:Captex ® 100:Labrasol ™, (1:1:1) | 40% | Purified Water, USP | Cloudy white liquid, immediate dispersion | No pellet formation, no oily residue |
| Capryol ™ 90:Captex ® 100:Labrasol ™, (1:1:1) | 40% | 0.01N HCl | Cloudy white liquid, immediate dispersion | No pellet formation, oily residue at bottom |
| Capryol ™ 90:Captex ® 100:Labrasol ™, (1:1:1) | 50% | 0.01N HCl | Milky white liquid, precipitation, oily residue | No pellet formation, oily residue at bottom |
| Capryol ™ 90:Captex ® 100:Labrasol ™, (1:1:1) | 50% | Purified Water, USP | Milky white liquid, precipitation, oily residue | No pellet formation, oily residue at bottom |
| Capryol ™ 90:Captex ® 100:Labrasol ™, (56:22:22) | 25% | Purified Water, USP | Milky white liquid, immediate emulsion | No pellet formation, no oily residue |
| Capryol ™ 90:Captex ® 100:Labrasol ™, (56:22:22) | 25% | 0.01N HCl | Milky white liquid, immediate emulsion | No pellet formation, no oily residue |
| Capryol ™ 90:Captex ® 100:Labrasol ™, (56:22:22) | 30% | Purified Water, USP | Cloudy white liquid, immediate dispersion | No pellet formation, oily residue at bottom |
| Capryol ™ 90:Captex ® 100:Labrasol ™, (56:22:22) | 30% | 0.01N HCl | Hazy liquid, delayed dispersion | No pellet formation, oily residue at bottom |
| Capryol ™ 90:Captex ® 100:Labrasol ™, (56:22:22) | 40% | Purified Water, USP | Hazy liquid, delayed dispersion | No pellet formation, oily residue at bottom |
| Capryol ™ 90:Captex ® 100:Labrasol ™, (56:22:22) | 40% | 0.01N HCl | Clear solution, oily residue | No pellet formation, oily residue at bottom |

TABLE 12-continued

Observations upon Dilution of Mitotane Systems

| System (expressed as w/w) | Drug Loading | Dilution (1:200 v/v) | Observations after Dilution | Observations after Centrifugation |
|---|---|---|---|---|
| Capryol ™ 90:Captex ® 100:Labrasol ™, (56:22:22) | 50% | Purified Water, USP | Clear solution, precipitation, oily residue | Pellet formation (precipitate) |
| Capryol ™ 90:Captex ® 100:Labrasol ™, (56:22:22) | 50% | 0.01N HCl | Clear solution, precipitation, oily residue | Pellet formation (precipitate) |
| Capryol ™ 90:Captex ® 100:Labrasol ™:Polysorbate 80, (1:1:1):1 | 25% | Purified Water, USP | Milky white liquid, immediate dispersion | No pellet formation, hazy liquid |
| Capryol ™ 90:Captex ® 100:Labrasol ™:Polysorbate 80, (1:1:1):1 | 25% | 0.01N HCl | Milky white liquid, immediate dispersion | No pellet formation, hazy liquid |
| Capryol ™ 90:Captex ® 100:Labrasol ™:Polysorbate 80, (1:1:1):1 | 50% | Purified Water, USP | Milky white liquid, immediate dispersion, emulsion breaking | No pellet formation, gel residue |
| Capryol ™ 90:Captex ® 100:Labrasol ™:Polysorbate 80, (1:1:1):1 | 50% | 0.01N HCl | Milky white liquid, immediate dispersion, emulsion breaking | No pellet formation, gel residue |
| Capryol ™ 90:Captex ® 100:Polysorbate 80, (1:1:1) | 25% | Purified Water, USP | Milky white liquid, immediate dispersion | No pellet formation, oily reside at bottom (excessive) |
| Capryol ™ 90:Captex ® 100:Polysorbate 80, (1:1:1) | 25% | 0.01N HCl | Milky white liquid, immediate dispersion | No pellet formation, oily reside at bottom (excessive) |
| Capryol ™ 90:Captex ® 100:Polysorbate 80, (1:1:1) | 50% | Purified Water, USP | Cloudy white liquid, immediate dispersion | No pellet formation, oily reside at bottom (excessive) |
| Capryol ™ 90:Captex ® 100:Polysorbate 80, (1:1:1) | 50% | 0.01N HCl | Cloudy white liquid, immediate dispersion | No pellet formation, oily reside at bottom (excessive) |
| Capryol ™ 90:Captex ® 100:Polysorbate 80, (56:22:22) | 25% | Purified Water, USP | Cloudy white liquid, immediate dispersion | No pellet formation, oily reside at bottom (excessive) |
| Capryol ™ 90:Captex ® 100:Polysorbate 80, (56:22:22) | 25% | 0.01N HCl | Cloudy white liquid, immediate dispersion | No pellet formation, oily reside at bottom (excessive) |
| Capryol ™ 90:Captex ® 100:Polysorbate 80, (56:22:22) | 50% | Purified Water, USP | Milky white liquid, immediate dispersion | No pellet formation, oily reside at bottom (excessive) |
| Capryol ™ 90:Captex ® 100:Polysorbate 80, (56:22:22) | 50% | 0.01N HCl | Milky white liquid, immediate dispersion | No pellet formation, oily reside at bottom (excessive) |
| Captex ® 100:Polysorbate 80:Triethyl Citrate:(1:1:1) | 25% | Purified Water, USP | Milky white liquid, immediate dispersion | No pellet formation, oily residue at bottom (excessive) |
| Captex ® 100:Capryol ™ 90:Labrasol ™, (56:22:22) | 25% | 0.01N HCl | Milky white liquid, immediate emulsion | No pellet formation, oily residue at bottom |
| Captex ® 100:Capryol ™ 90:Labrasol ™, (56:22:22) | 30% | Purified Water, USP | Cloudy white liquid, immediate dispersion | No pellet formation, no oily residue |
| Captex ® 100:Capryol ™ 90:Labrasol ™, (56:22:22) | 30% | 0.01N HCl | Cloudy white liquid, immediate dispersion | No pellet formation, oily residue at bottom |
| Captex ® 100:Capryol ™ 90:Labrasol ™, (56:22:22) | 40% | Purified Water, USP | Cloudy white liquid, immediate dispersion | No pellet formation, oily residue at bottom |
| Captex ® 100:Capryol ™ 90:Labrasol ™, (56:22:22) | 40% | 0.01N HCl | Cloudy white liquid, immediate dispersion | Drug crystals- rod shaped side of the tube (very few crystals) |
| Captex ® 100:Capryol ™ 90:Labrasol ™, (56:22:22) | 50% | Purified Water, USP | Clear solution, precipitation, oily residue | Pellet formation (semi-solid) |
| Captex ® 100:Capryol ™ 90:Labrasol ™, (56:22:22) | 50% | 0.01N HCl | Clear solution, precipitation, oily residue | Pellet formation (semi-solid) |
| Captex ® 100:Capryol ™ 90:Labrasol ™, (56:22:22)* | 25% | Purified Water, USP | Milky white liquid, immediate emulsion | No pellet formation, oily residue at bottom |
| Captex ® 100:Capryol ™ 90:Polysorbate 80, (56:22:22) | 25% | Purified Water, USP | Cloudy white liquid, immediate dispersion | No pellet formation, oily reside at bottom (excessive) |
| Captex ® 100:Capryol ™ 90:Polysorbate 80, (56:22:22) | 25% | 0.01N HCl | Cloudy white liquid, immediate dispersion | No pellet formation, oily reside at bottom (excessive) |
| Captex ® 100:Capryol ™ 90:Polysorbate 80, (56:22:22) | 50% | Purified Water, USP | Milky white liquid, immediate dispersion | No pellet formation, oily reside at bottom (excessive) |

TABLE 12-continued

Observations upon Dilution of Mitotane Systems

| System (expressed as w/w) | Drug Loading | Dilution (1:200 v/v) | Observations after Dilution | Observations after Centrifugation |
|---|---|---|---|---|
| Captex ® 100:Capryol ™ 90:Polysorbate 80, (56:22:22) | 50% | 0.01N HCl | Milky white liquid, immediate dispersion | No pellet formation, oily reside at bottom (excessive) |
| Captex ® 100:Labrasol ™:Triethyl Citrate, (1:1:1) | 25% | Purified Water, USP | Cloudy white liquid, immediate dispersion, oily residue | No pellet formation, no oily residue |
| Captex ® 100:Labrasol ™:Triethyl Citrate, (1:1:1) | 25% | 0.01N HCl | Cloudy white liquid, immediate dispersion, oily residue | No pellet formation, no oily residue |
| Captex ® 100:Labrasol ™:Triethyl Citrate, (1:1:1) | 50% | Purified Water, USP | Cloudy white liquid, delayed dispersion, oily residue | No pellet formation, no oily residue |
| Captex ® 100:Labrasol ™:Triethyl Citrate, (1:1:1) | 50% | 0.01N HCl | Milky white liquid, delayed dispersion, oily residue | Pellet formation (semi-solid) |
| Captex ® 100:Labrasol ™:Triethyl Citrate, (56:22:22) | 25% | Purified Water, USP | Hazy liquid, delayed dispersion, oily residue | No pellet formation, oily residue at bottom |
| Captex ® 100:Labrasol ™:Triethyl Citrate, (56:22:22) | 25% | 0.01N HCl | Cloudy white liquid, immediate dispersion, oily residue | No pellet formation, oily residue at bottom |
| Captex ® 100:Labrasol ™:Triethyl Citrate, (56:22:22) | 50% | Purified Water, USP | Cloudy white liquid, delayed dispersion, oily residue | Drug crystals- rod shaped side of the tube (very few crystals) |
| Captex ® 100:Labrasol ™:Triethyl Citrate, (56:22:22) | 50% | 0.01N HCl | Cloudy white liquid, delayed dispersion, oily residue | Pellet formation (precipitation) |
| Captex ® 100:Polysorbate 80:Triethyl Citrate, (56:22:22) | 25% | Purified Water, USP | Milky white liquid, immediate dispersion | No pellet formation, oily residue at bottom (excessive) |
| Captex ® 100:Polysorbate 80:Triethyl Citrate, (56:22:22) | 25% | 0.01N HCl | Milky white liquid, immediate dispersion | Pellet formation (semi-solid) |
| Captex ® 100:Polysorbate 80:Triethyl Citrate, (1:1:1) | 50% | Purified Water, USP | Milky white liquid, immediate dispersion, oily residue | Pellet formation (semi-solid) |
| Captex ® 100:Polysorbate 80:Triethyl Citrate, (1:1:1) | 50% | 0.01N HCl | Milky white liquid, immediate dispersion, oily residue | Pellet formation (semi-solid) |
| Labrasol ™:Capryol ™ 90:Captex ® 100, 22:22:56 | 25% | Purified Water, USP | Milky white liquid, immediate emulsion | No pellet formation, oily residue at bottom |
| Labrasol ™:Capryol ™ 90:Captex ® 100, 22:22:56 | 25% | 0.01N HCl | Milky white liquid, immediate emulsion | No pellet formation, oily residue at bottom |
| Labrasol ™:Capryol ™ 90:Captex ® 100, (56:22:22) | 30% | Purified Water, USP | Milky white liquid, immediate dispersion, oily residue | No pellet formation, oily residue at bottom |
| Labrasol ™:Capryol ™ 90:Captex ® 100, (56:22:22) | 30% | 0.01N HCl | Milky white liquid, immediate dispersion, oily residue | No pellet formation, no oily residue |
| Labrasol ™:Capryol ™ 90:Captex ® 100, (56:22:22) | 40% | Purified Water, USP | Milky white liquid, immediate dispersion | Pellet formation (semi-solid) |
| Labrasol ™:Capryol ™ 90:Captex ® 100, (56:22:22) | 40% | 0.01N HCl | Milky white liquid, immediate dispersion, oily residue | Pellet formation (semi-solid) |
| Labrasol ™:Capryol ™ 90:Captex ® 100, (56:22:22) | 50% | Purified Water, USP | Clear solution, precipitation, oily residue | Pellet formation (semi-solid) |
| Labrasol ™:Capryol ™ 90:Captex ® 100, (56:22:22) | 50% | 0.01N HCl | Clear solution, precipitation, oily residue | Pellet formation (semi-solid) |
| Labrasol ™:Captex ® 100:Triethyl Citrate, (56:22:22) | 25% | Purified Water, USP | Cloudy white liquid, immediate dispersion, oily residue | No pellet formation, no oily residue |
| Labrasol ™:Captex ® 100:Triethyl Citrate, (56:22:22) | 25% | 0.01N HCl | Milky white liquid, immediate dispersion, oily residue | No pellet formation, no oily residue |
| Labrasol ™:Captex ® 100:Triethyl Citrate, (56:22:22) | 50% | Purified Water, USP | Milky white liquid, immediate dispersion, oily residue | Pellet formation (semi-solid) |
| Labrasol ™:Captex ® 100:Triethyl Citrate, (56:22:22) | 50% | 0.01N HCl | Cloudy white liquid, delayed dispersion, oily residue | Pellet formation (semi-solid) |
| Polysorbate 80:Capryol ™ 90:Captex ® 100, (56:22:22) | 25% | Purified Water, USP | Milky white liquid, immediate dispersion | No pellet formation, oily reside at bottom (excessive) |

TABLE 12-continued

Observations upon Dilution of Mitotane Systems

| System (expressed as w/w) | Drug Loading | Dilution (1:200 v/v) | Observations after Dilution | Observations after Centrifugation |
|---|---|---|---|---|
| Polysorbate 80:Capryol ™ 90:Captex ® 100, (56:22:22) | 25% | 0.01N HCl | Milky white liquid, immediate dispersion | No pellet formation, oily reside at bottom (excessive) |
| Polysorbate 80:Capryol ™ 90:Captex ® 100, (56:22:22) | 50% | Purified Water, USP | Milky white liquid, immediate dispersion | Pellet formation (semi-solid) |
| Polysorbate 80:Capryol ™ 90:Captex ® 100, (56:22:22) | 50% | 0.01N HCl | Milky white liquid, immediate dispersion | Pellet formation (semi-solid) |
| Polysorbate 80:Captex ® 100:Triethyl Citrate, (56:22:22) | 50% | Purified Water, USP | Milky white liquid, immediate dispersion, oily residue | Pellet formation (semi-solid) |
| Polysorbate 80:Captex ® 100:Triethyl Citrate, (56:22:22) | 50% | 0.01N HCl | Milky white liquid, immediate dispersion, oily residue | Pellet formation (semi-solid) |
| Polysorbate 80:Captex ® 100:Triethyl Citrate, (56:22:22) | 25% | 0.01N HCl | Milky white liquid, immediate dispersion | Pellet formation (semi-solid) |
| Polysorbate 80:Captex ® 100:Triethyl Citrate, (56:22:22) | 25% | 0.01N HCl | Milky white liquid, immediate dispersion | No pellet formation, oily residue at bottom (excessive) |
| Polysorbate 80:Captex ® 100:Triethyl Citrate, (56:22:22) | 25% | Purified Water, USP | Milky white liquid, immediate dispersion | Pellet formation (semi-solid) |
| Polysorbate 80:Captex ® 100:Triethyl Citrate, (56:22:22) | 50% | Purified Water, USP | Milky white liquid, immediate dispersion, oily residue | Pellet formation (semi-solid) |
| Polysorbate 80:Captex ® 100:Triethyl Citrate, (56:22:22) | 50% | 0.01N HCl | Milky white liquid, immediate dispersion, oily residue | Pellet formation (semi-solid) |
| Triethyl Citrate:Captex ® 100:Labrasol ™, (56:22:22) | 25% | Purified Water, USP | Hazy liquid, immediate dispersion, oily residue | No pellet formation, no oily residue |
| Triethyl Citrate:Captex ® 100:Labrasol ™, (56:22:22) | 50% | Purified Water, USP | Hazy liquid, delayed dispersion, oily residue | Pellet formation (semi-solid) |
| Triethyl Citrate:Captex ® 100:Labrasol ™, (56:22:22) | 50% | 0.01N HCl | Cloudy white liquid, delayed dispersion, oily residue | Pellet formation (semi-solid) |
| Triethyl Citrate:Captex ® 100:Labrasol ™, (56:22:22) | 25% | 0.01N HCl | Hazy liquid, delayed dispersion, oily residue | No pellet formation, no oily residue |
| Triethyl Citrate:Captex ® 100:Polysorbate 80 (56:22:22) | 50% | Purified Water, USP | Milky white liquid, immediate dispersion, oily residue | Pellet formation (semi-solid) |
| Triethyl Citrate:Captex ® 100:Polysorbate 80 (56:22:22)* | 50% | 0.01N HCl | Milky white liquid, immediate dispersion, oily residue | Pellet formation (semi-solid) |
| Triethyl Citrate:Captex ® 100:Polysorbate 80, (56:22:22) | 25% | Purified Water, USP | Cloudy white liquid, immediate dispersion | Pellet formation (semi-solid) |
| Triethyl Citrate:Captex ® 100:Polysorbate 80, (56:22:22) | 25% | 0.01N HCl | Cloudy white liquid, immediate dispersion | No pellet formation, oily residue at bottom (excessive) |

The highest mitotane concentration trial that was found to be the most stable was 28.5% weight/weight, or 40% drug loading (28.5/(100-28.5)=40% drug loading).

Due to the drug precipitation overnight in some samples, selected systems were retested at 50% and 55% drug loading in a direct loading solubility study.

TABLE 13

Dynamic Light Scattering of Supernatant Liquids

| System (expressed as w/w) | Drug Loading | Dilution 1:200 (v/v) | Intensity Diameter (Gaussian) nm | Standard Deviation nm | Chi$^2$ | Decay | Fit Error |
|---|---|---|---|---|---|---|---|
| Capryol ™ 90:Captex ® 100:Labrasol ™, (1:1:1) | 25% | Purified Water, USP | 149.49 | 78.03 | 2.299 | 2.172 | 5.105 |
| Capryol ™ 90:Captex ® 100:Labrasol ™, (1:1:1) | 25% | 0.01N HCl | 251.24 | 96.22 | 3.139 | 2.355 | 8.831 |
| Capryol ™ 90:Captex ® 100:Labrasol ™, (1:1:1) | 50% | Purified Water, USP | 192.04 | 46.47 | 0.34 | 2.599 | 11.317 |
| Capryol ™ 90:Captex ® 100:Labrasol ™, (1:1:1) | 50% | 0.01N HCl | 579.06 | 216.57 | 6.344 | 2.408 | 5.511 |

TABLE 13-continued

Dynamic Light Scattering of Supernatant Liquids

| System (expressed as w/w) | Drug Loading | Dilution 1:200 (v/v) | Intensity Diameter (Gaussian) nm | Standard Deviation nm | Chi$^2$ | Decay | Fit Error |
|---|---|---|---|---|---|---|---|
| Capryol ™ 90:Captex ® 100:Labrasol ™, (56:22:22) | 25% | Purified Water, USP | 246.63 | 148.72 | 6.079 | 2.394 | 5.655 |
| Capryol ™ 90:Captex ® 100:Labrasol ™, (56:22:22) | 25% | 0.01N HCl | 399.85 | 170.34 | 1.91 | 2.532 | 10.43 |
| Capryol ™ 90:Captex ® 100:Labrasol ™, (56:22:22) | 50% | Purified Water, USP | 197.87 | 50.06 | 1.142 | 2.431 | 22.115 |
| Capryol ™ 90:Captex ® 100:Labrasol ™, (56:22:22) | 50% | 0.01N HCl | 380.41 | 159.52 | 0.883 | 2.33 | 15.389 |
| Capryol ™ 90:Captex ® 100:Labrasol ™:Polysorbate 80, (1:1:1:1) | 25% | Purified Water, USP | 148.99 | 89.24 | 2.885 | 2.435 | 6.165 |
| Capryol ™ 90:Captex ® 100:Labrasol ™:Polysorbate 80, (1:1:1:1) | 25% | 0.01N HCl | 153.44 | 94.52 | 6.007 | 2.363 | 8.267 |
| Capryol ™ 90:Captex ® 100:Labrasol ™:Polysorbate 80, (1:1:1:1) | 50% | Purified Water, USP | 249.86 | 176.15 | 104.628 | 2.439 | 6.835 |
| Capryol ™ 90:Captex ® 100:Labrasol ™:Polysorbate 80, (1:1:1:1) | 50% | 0.01N HCl | 273.31 | 209.08 | 122.608 | 2.372 | 6.275 |
| Capryol ™ 90:Captex ® 100:Polysorbate 80, (1:1:1) | 25% | Purified Water, USP | 120.82 | 55.94 | 2.273 | 2.37 | 9.598 |
| Capryol ™ 90:Captex ® 100:Polysorbate 80, (1:1:1) | 25% | 0.01N HCl | 138.62 | 61.96 | 1.725 | 2.48 | 7.598 |
| Capryol ™ 90:Captex ® 100:Polysorbate 80, (1:1:1) | 50% | Purified Water, USP | 93.68 | 36.44 | 1.307 | 2.439 | 10.223 |
| Capryol ™ 90:Captex ® 100:Polysorbate 80, (1:1:1) | 50% | 0.01N HCl | 81.03 | 36.95 | 5.457 | 2.351 | 4.614 |
| Capryol ™ 90:Captex ® 100:Polysorbate 80, (56:22:22) | 25% | Purified Water, USP | 131.31 | 71.56 | 23.15 | 2.484 | 7.392 |
| Capryol ™ 90:Captex ® 100:Polysorbate 80, (56:22:22) | 25% | 0.01N HCl | 392.44 | 313.95 | 133.58 | 2.45 | 5.42 |
| Capryol ™ 90:Captex ® 100:Polysorbate 80, (56:22:22) | 50% | Purified Water, USP | 104.48 | 57.36 | 11.872 | 2.558 | 10.424 |
| Capryol ™ 90:Captex ® 100:Polysorbate 80, (56:22:22) | 50% | 0.01N HCl | 143.95 | 82.05 | 36.573 | 2.52 | 9.186 |
| Captex ® 100:Capryol ™ 90:Polysorbate 80, (56:22:22) | 25% | Purified Water, USP | 127.65 | 66.88 | 2.57 | 2.395 | 7.469 |
| Captex ® 100:Capryol ™ 90:Polysorbate 80, (56:22:22) | 25% | 0.01N HCl | 225.36 | 159.55 | 37.175 | 2.809 | 8.54 |
| Captex ® 100:Capryol ™ 90:Polysorbate 80, (56:22:22) | 50% | Purified Water, USP | 125.84 | 70.47 | 10.714 | 2.411 | 8.912 |
| Captex ® 100:Capryol ™ 90:Polysorbate 80, (56:22:22) | 50% | 0.01N HCl | 138.68 | 83.76 | 9.857 | 2.624 | 8.937 |
| Captex ® 100:Labrasol ™:Triethyl Citrate, (1:1:1) | 50% | 0.01N HCl | 1080.6 | 637.55 | 14.632 | 2.491 | 1793.64 |
| Captex ® 100:Labrasol ™:Triethyl Citrate, (56:22:22) | 25% | Purified Water, USP | 142.51 | 44.03 | 0.44 | 2.551 | 13.836 |
| Captex ® 100:Labrasol ™:Triethyl Citrate (1:1:1) | 25% | Purified Water, USP | 136.98 | 35.2 | 1.919 | 2.513 | 20.442 |
| Captex ® 100:Polysorbate 80:Triethyl Citrate, (1:1:1) | 25% | Purified Water, USP | 131.92 | 54.48 | 2.263 | 2.455 | 7.245 |
| Captex ® 100:Polysorbate 80:Triethyl Citrate, (1:1:1) | 25% | 0.01N HCl | 127 | 82.27 | 0.999 | 2.561 | 10.035 |
| Captex ® 100:Polysorbate 80:Triethyl Citrate, (1:1:1) | 50% | Purified Water, USP | 98.43 | 52.27 | 4.069 | 2.518 | 7.942 |
| Captex ® 100:Polysorbate 80:Triethyl Citrate, (1:1:1) | 50% | 0.01N HCl | 103.26 | 54.11 | 2.981 | 2.587 | 7.047 |
| Captex ® 100:Polysorbate 80:Triethyl Citrate, (56:22:22) | 25% | Purified Water, USP | 126.43 | 62.08 | 1.564 | 2.886 | 5.675 |
| Captex ® 100:Polysorbate 80:Triethyl Citrate, (56:22:22) | 25% | 0.01N HCl | 139.7 | 77.11 | 5.804 | 2.46 | 9.841 |
| Captex ® 100:Polysorbate 80:Triethyl Citrate, (56:22:22) | 50% | Purified Water, USP | 126.67 | 70.05 | 1.874 | 2.415 | 7.452 |
| Captex ® 100:Polysorbate 80:Triethyl Citrate, (56:22:22) | 50% | 0.01N HCl | 117.53 | 60.17 | 0.971 | 2.443 | 6.369 |
| Captex ® 100:Capryol ™ 90:Labrasol ™, (56:22:22) | 50% | Purified Water, USP | 213.42 | 45.03 | 0.93 | 2.356 | 5.465 |
| Captex ® 100:Capryol ™ 90:Labrasol ™, (56:22:22) | 50% | 0.01N HCl | 569.76 | 394.84 | 1.358 | 2.361 | 10.067 |
| Captex ® 100:Capryol ™ 90:Labrasol ™, (56:22:22) | 25% | Purified Water, USP | 547.98 | 415.92 | 42.277 | 2.343 | 3.88 |

TABLE 13-continued

Dynamic Light Scattering of Supernatant Liquids

| System (expressed as w/w) | Drug Loading | Dilution 1:200 (v/v) | Intensity Diameter (Gaussian) nm | Standard Deviation nm | Chi$^2$ | Decay | Fit Error |
|---|---|---|---|---|---|---|---|
| Captex ® 100:Capryol ™ 90:Labrasol ™, (56:22:22) | 25% | 0.01N HCl | 640.09 | 410.3 | 15.47 | 2.37 | 5.327 |
| Captex ®100:Labrasol ™:Triethyl Citrate, (56:22:22) | 25% | 0.01N HCl | 512.67 | 309.65 | 28.203 | 2.595 | 5.787 |
| Captex ® 100:Labrasol ™:Triethyl Citrate, (56:22:22) | 50% | Purified Water, USP | 151.03 | 24.62 | 0.855 | 2.403 | 9.435 |
| Captex ®100:Labrasol ™:Triethyl Citrate, (1:1:1) | 25% | 0.01N HCl | 967.49 | 521.47 | 17.912 | 2.579 | 1843.23 |
| Captex ®100:Labrasol ™:Triethyl Citrate, (56:22:22) | 50% | 0.01N HCl | 1256.38 | 741.27 | 116.546 | 2.107 | 1572.65 |
| Labrasol ™:Capryol ™ 90:Captex ® 100, (56:22:22) | 25% | Purified Water, USP | 121.46 | 50.77 | 1.4 | 2.522 | 6.999 |
| Labrasol ™:Capryol ™ 90:Captex ® 100, (56:22:22) | 25% | 0.01N HCl | 267.43 | 23.27 | 0.185 | 3.067 | 9.94 |
| Labrasol ™:Capryol ™ 90:Captex ® 100, (56:22:22) | 50% | Purified Water, USP | 162.18 | 24.65 | 0.652 | 2.498 | 11.071 |
| Labrasol ™:Capryol ™ 90:Captex ® 100, (56:22:22) | 50% | 0.01N HCl | 2140.74 | 1485.67 | 7.137 | 1.821 | 1506.17 |
| Labrasol ™:Captex ® 100:Triethyl Citrate, (56:22:22) | 25% | Purified Water, USP | 119.93 | 20.51 | 1.825 | 2.387 | 12.02 |
| Labrasol ™:Captex ® 100:Triethyl Citrate, (56:22:22) | 50% | 0.01N HCl | 281.59 | 144.74 | 0.449 | 2.448 | 6.331 |
| Labrasol ™:Captex ® 100:Triethyl Citrate, (56:22:22) | 50% | Purified Water, USP | 171.38 | 71.64 | 1.226 | 2.451 | 8.004 |
| Labrasol ™:Captex ® 100:Triethyl Citrate, (56:22:22) | 25% | 0.01N HCl | 858.78 | 490.36 | 18.004 | 2.236 | 1476.04 |
| Polysorbate 80:Capryol ™ 90:Captex ® 100, (56:22:22) | 25% | Purified Water, USP | 116.29 | 51.52 | 1.541 | 2.466 | 8.594 |
| Polysorbate 80:Capryol ™ 90:Captex ® 100, (56:22:22) | 25% | Purified Water, USP | 116.29 | 51.52 | 1.541 | 2.4665 | 8.594 |
| Polysorbate 80:Capryol ™ 90:Captex ® 100,(56:22:22) | 25% | 0.01N HCl | 93.68 | 36.44 | 1.307 | 2.439 | 10.233 |
| Polysorbate 80:Capryol ™ 90:Captex ® 100, (56:22:22) | 50% | Purified Water, USP | 101.75 | 33.07 | 0.635 | 2.438 | 8.903 |
| Polysorbate 80:Capryol ™ 90:Captex ® 100, (56:22:22) | 50% | 0.01N HCl | 100.78 | 20.96 | 0.599 | 2.463 | 8.643 |
| Polysorbate 80:Captex ® 100:Triethyl Citrate, (56:22:22) | 25% | Purified Water, USP | 104.37 | 51.87 | 1.281 | 2.376 | 8.822 |
| Polysorbate 80:Captex ® 100:Triethyl Citrate, (56:22:22) | 25% | 0.01N HCl | 106.35 | 31.59 | 1.422 | 2.517 | 15.046 |
| Polysorbate 80:Captex ® 100:Triethyl Citrate, (56:22:22) | 50% | Purified Water, USP | 110.01 | 49.17 | 0.462 | 2.44 | 7.309 |
| Polysorbate 80:Captex ® 100:Triethyl Citrate, (56:22:22) | 50% | 0.01N HCl | 114.97 | 37.59 | 7.5 | 2.492 | 11.166 |
| Triethyl Citrate:Captex ® 100:Labrasol ™, (1:1:1) | 50% | Purified Water, USP | 136.66 | 16.67 | 0.814 | 2.523 | 9.782 |
| Triethyl Citrate:Captex ® 100:Labrasol ™, (56:22:22) | 25% | Purified Water, USP | 154.92 | 84.59 | 4.659 | 2.357 | 11.19 |
| Triethyl Citrate:Captex ® 100:Labrasol ™, (56:22:22) | 25% | 0.01N HCl | 541.6 | 298.96 | 2.746 | 2.654 | 5.985 |
| Triethyl Citrate:Captex ® 100:Labrasol ™, (56:22:22) | 50% | Purified Water, USP | 158.37 | 46.09 | 1.002 | 2.29 | 14.573 |
| Triethyl Citrate:Captex ® 100:Labrasol ™, (56:22:22) | 50% | 0.01N HCl | 965.26 | 412.17 | 0.862 | 2.77 | 2314.71 |
| Triethyl Citrate:Captex ® 100:Polysorbate 80, (56:22:22) | 25% | Purified Water, USP | 126.57 | 77.33 | 7.996 | 2.71 | 10.059 |
| Triethyl Citrate:Captex ® 100:Polysorbate 80, (56:22:22) | 25% | 0.01N HCl | 112.11 | 44.17 | 0.686 | 2.388 | 6.75 |
| Triethyl Citrate:Captex ® 100:Polysorbate 80, (56:22:22) | 50% | Purified Water, USP | 164.69 | 102.6 | 3.606 | 2.318 | 6.345 |
| Triethyl Citrate:Captex ® 100:Polysorbate 80, (56:22:22) | 50% | 0.01N HCl | 187.73 | 121.09 | 18.036 | 2.642 | 7.277 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of increasing the bioavailability of mitotane comprising preparing a formulation comprising (a) between 33% and 67% (w/w) mitotane, (b) 10-30% (w/w) polysorbate, (c) 10-30% (w/w) propylene glycol monocaprylate, and (d) 20-60% (w/w) propylene glycol dicaprate, wherein the formulation is substantially free of a polar solvent, and administering the formulation to a host.

2. The method of claim 1, wherein the formulation comprises between 37% and 54% (w/w) mitotane.

3. The method of claim 2, wherein the formulation comprises about 50% (w/w) mitotane.

4. The method of claim 1, wherein the formulation comprises 15-20% (w/w) propylene glycol monocaprylate, 35-50% (w/w) propylene glycol dicaprate, and 15-20% (w/w) polysorbate.

5. The method of claim 2 wherein the formulation comprises 15-17% (w/w) propylene glycol monocaprylate, 38-42% (w/w) propylene glycol dicaprate, and 15-17% (w/w) polysorbate.

6. The method of claim 1 wherein the polysorbate is selected from the group consisting of polysorbate 20, polysorbate 40, polysorbate 60, polysorbate 65, polysorbate 80, and mixtures thereof.

7. The method of claim 6, wherein the polysorbate is polysorbate 80.

* * * * *